(12) United States Patent
Tawfick et al.

(10) Patent No.: US 11,060,512 B2
(45) Date of Patent: Jul. 13, 2021

(54) ELONGATE FIBER ARTIFICIAL MUSCLES AND METHOD OF FABRICATION

(71) Applicant: The Board of Trustees of the University of Illinois, Urbana, IL (US)

(72) Inventors: Sameh H. Tawfick, Champaign, IL (US); Caterina Lamuta, Iowa City, IA (US)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

(21) Appl. No.: 16/573,398

(22) Filed: Sep. 17, 2019

(65) Prior Publication Data

US 2020/0088174 A1 Mar. 19, 2020

Related U.S. Application Data

(60) Provisional application No. 62/732,273, filed on Sep. 17, 2018.

(51) Int. Cl.
*F03G 7/06* (2006.01)
*C03C 25/32* (2018.01)

(52) U.S. Cl.
CPC ............... *F03G 7/06* (2013.01); *C03C 25/32* (2013.01)

(58) Field of Classification Search
CPC ........ A61F 2/14; A61F 2/1635; A61F 2/1624; A61F 2/08; A61F 2/1627;
(Continued)

(56) References Cited

U.S. PATENT DOCUMENTS

2004/0263028 A1* 12/2004 Pei .................... H01G 5/16
310/307
2006/0261709 A1* 11/2006 Kato ................... F03G 7/06
310/367
(Continued)

FOREIGN PATENT DOCUMENTS

KR 2017039849 A * 4/2017

OTHER PUBLICATIONS

English Abstractor KR 2017039849 A, Apr. 2017.*
(Continued)

*Primary Examiner* — Mark A Laurenzi
*Assistant Examiner* — Mickey H France
(74) *Attorney, Agent, or Firm* — Greer, Burns & Crain, Ltd.; Steven P. Fallon

(57) ABSTRACT

An elongate fiber artificial muscle includes or consists of an elongate carbon or glass fiber and at least a partial coating of a polymer, and preferably a full shell coating to form a core-shell arrangement, that is volumetrically responsive to thermal changes or to moisture changes. Additional elongate fiber artificial muscles of the invention include a plurality of elongate carbon or glass fibers that are infiltrated between the fibers with a polymer that is volumetrically responsive to thermal changes or to moisture changes. In a fabrication method, the rheology (flow characteristic) of a polymer precursor is adjusted with solvent so it is less viscous. A fiber or plurality of fibers (pre-twisted or untwisted), such as a tow is dipped in the polymer precursor. The fiber or fibers is then pulled out of the polymer precursor and hung to allow polymer to distribute and then cured and can be twisted to coil prior to curing. A model is provided to fabricate elongate fiber artificial muscle with specific characteristics based upon a thermal or moisture expansion coefficient of
(Continued)

the polymer, its elongation capability percentage before flaking or breaking, and its elastic modulus.

22 Claims, 9 Drawing Sheets

(58) Field of Classification Search
CPC ..... A61F 2250/0002; A61F 2002/0894; F03G 7/06; F03G 7/065
USPC .................................................. 60/527–529
See application file for complete search history.

(56) References Cited

U.S. PATENT DOCUMENTS

| | | | |
|---|---|---|---|
| 2013/0153246 A1* | 6/2013 | Carrejo .................. | F03G 7/065 166/381 |
| 2015/0152852 A1* | 6/2015 | Li ........................... | D01F 6/00 60/528 |
| 2016/0025079 A1* | 1/2016 | Li ........................... | F03G 7/06 60/528 |
| 2018/0102232 A1* | 4/2018 | Ma ......................... | H01H 61/04 |
| 2020/0216630 A1* | 7/2020 | Shan ....................... | C08K 3/08 |

OTHER PUBLICATIONS

Foroughi et al., "Torsional Carbon Nanotube Artificial Muscles", Science, Oct. 2011, pp. 494-497, vol. 334, No. 6055, American Association for the Advancement of Science, Washington, DC.

Chun et al., "Hybrid carbon nanotube yarn artificial muscle inspired by spider dragline silk", Nature Communications, 2014, pp. 1-9, vol. 5, No. 3322, Macmillan Publishers Limited.

Choy et al., "Negative Thermal Expansion in Oriented Crystalline Polymers", Journal of Polymer Science: Polymer Physics Edition, 1981, pp. 335-352, vol. 19, John Wiley & Sons, Inc.

Cheng et al., "Moisture-Activated Torsional Graphene-Fiber Motor", Advanced Materials, 2014, pp. 2909-2913, vol. 26, Wiley-VCH Verlag GmbH & Co. KGaA, Weinheim.

Bhat, Structure and Properties of High-Performance Fibers, 2017, pp. 38-78, Woodhead Publishing.

Aziz et al., "Controlled and Scalable Torsional Actuation of Twisted Nylon 6 Fiber", Journal of Polymer Science, Part B: Polymer Physics, 2016, pp. 1278-1286, vol. 54, Wiley Periodicals, Inc.

Zill et al., Differential Equations with Boundary-Value Problems, Seventh Edition, 2009, Cengage Learning, Inc.

Yip et al., "High-Performance Robotic Muscles from Conductive Nylon Sewing Thread", 2015 IEEE International Conference on Robotics and Automation, pp. 2313-2318, Seattle, Washington.

Naik et al., "Twisted impregnated yarns: elastic properties", Journal of Strain Analysis, 2000, pp. 83-91, vol. 35, No. 2, IMechE.

Mounier et al., "Evaluation of transverse elastic properties of fibers used in composite materials by laser resonant ultrasound spectroscopy", Proceedings of the Acoustics 2012 Nantes Conference, 2012, pp. 1247-1250, Nantes, France.

Mirvakili et al., "Niobium Nanowire Yarns and their Application as Artificial Muscles", Advanced Functional Materials, 2013, pp. 4311-4316, vol. 23, Wiley-VCH Verlag GmbH & Co. KGaA, Weinheim.

Liu et al., "Influences of heating temperature on mechanical properties of polydimethylsiloxane", Sensors and Actuators A, 2009, pp. 42-45, vol. 151, Elsevier B.V.

Lima et al., "Efficient, Absorption-Powered Artificial Muscles Based on Carbon Nanotube Hybrid Yarns", Small, 2015, pp. 3113-3118, vol. 11, No. 26, Wiley-VCH Verlag GmbH & Co. KGaA, Weinheim.

Lima et al., "Electrically, Chemically, and Photonically Powered Torsional and Tensile Actuation of Hybrid Carbon Nanotube Yarn Muscles", Science, Nov. 2012, pp. 928-932, vol. 338, No. 6109, American Association for the Advancement of Science.

Lee et al., "Carbon Nanotube Yarn-Based Glucose Sensing Artificial Muscle", Small, 2016, pp. 2085-2091, vol. 12, No. 15, Wiley-VCH Verlag GmbH & Co. KGaA, Weinheim.

Krucinska & Stypka, "Direct Measurement of the Axial Poisson's Ratio of Single Carbon Fibres", Composites Science and Technology, 1991, pp. 1-12, vol. 41, Elsevier Science Publishers Ltd, England.

Kim et al., "Thermal Expansion and Contraction of an Elastomer Stamp Causes Position-Dependent Polymer Patterns in Capillary Force Lithography", Applied Materials & Interfaces, 2011, pp. 4695-4702, vol. 3, American Chemical Society.

Kim et al., "Harvesting electrical energy from carbon nanotube yarn twist", Science, Aug. 2017, pp. 773-778, vol. 357, American Association for the Advancement of Science, Washington, DC.

Johnston et al., "Mechanical characterization of bulk Sylgard 184 for microfluidics and microengineering", Journal of Micromechanics and Microengineering, 2014, pp. 1-7, vol. 24, IOP Publishing Ltd, United Kingdom.

Huber et al., "The selection of mechanical actuators based on performance indices", Proceedings of the Royal Society A, 1997, pp. 2185-2205, vol. 453, No. 1965, The Royal Society, London, England.

Hopkins & Chamis, "A Unique Set of Micromechanics Equations for High-Temperature Metal Matrix Composites", Testing Technology of Metal Matrix Composites, 1988, pp. 159-176, American Society for Testing and Materials.

Haines et al., "Artificial Muscles from Fishing Line and Sewing Thread", Science, Feb. 2014, pp. 868-872, vol. 343, No. 6173, American Association for the Advancement of Science, Washington, DC.

Haines et al., "New twist on artificial muscles", PNAS, Oct. 2016, pp. 11709-11716, vol. 113, No. 42, National Academy of Sciences.

* cited by examiner

FIG. 4A
FIG. 4B
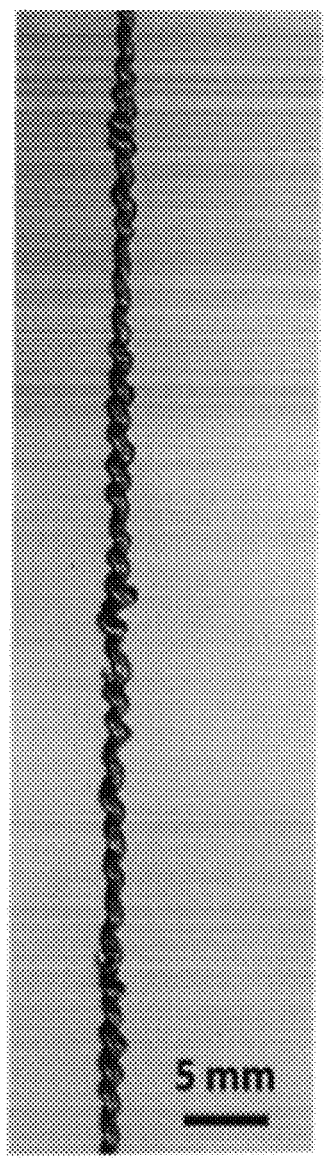
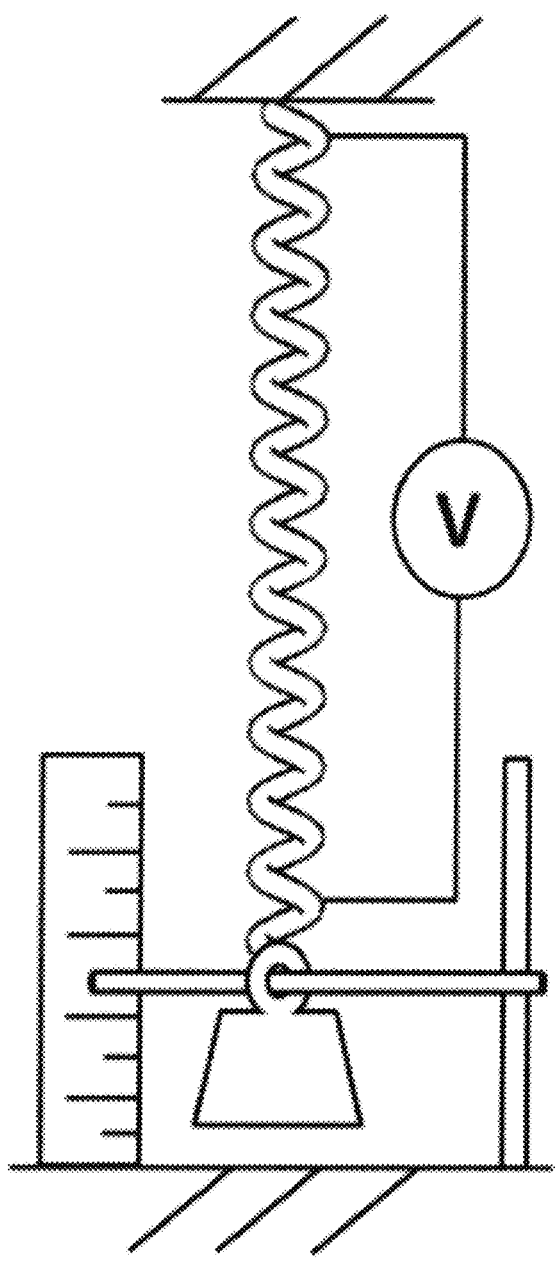

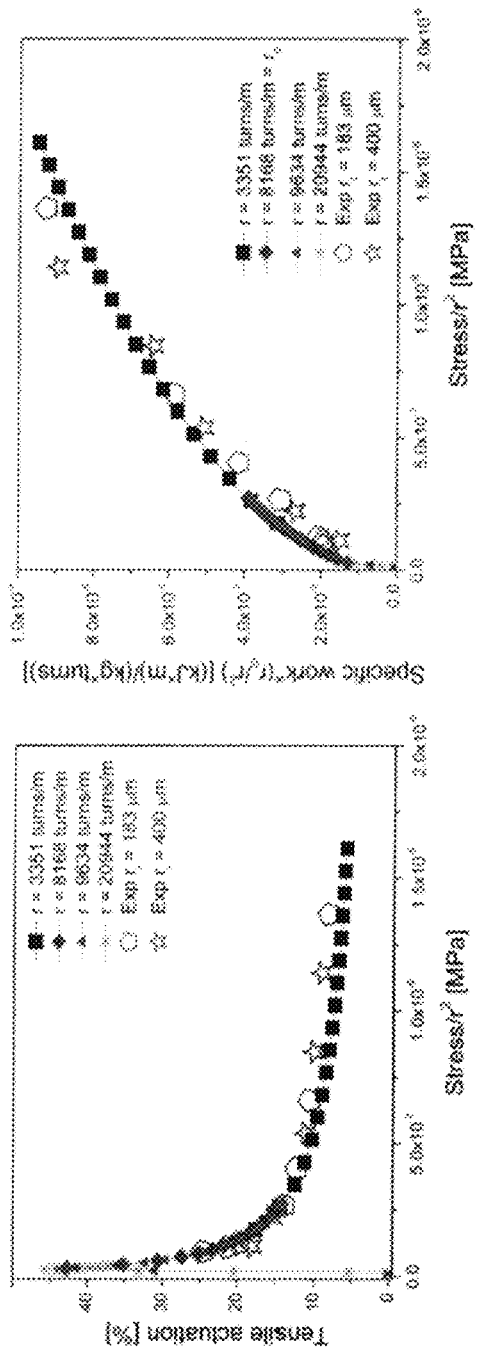
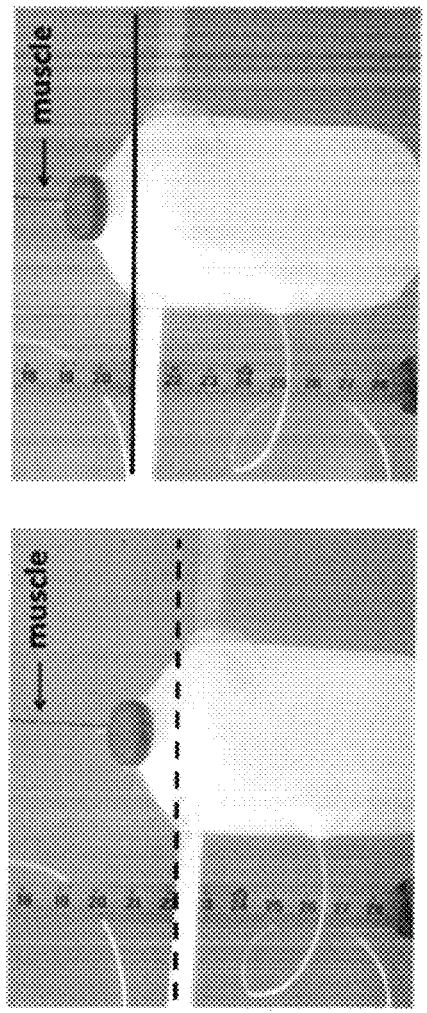
FIG. 8A
FIG. 8B
FIG. 8C

ELONGATE FIBER ARTIFICIAL MUSCLES AND METHOD OF FABRICATION

PRIORITY CLAIM AND REFERENCE TO RELATED APPLICATION

The application claims priority under 35 U.S.C. § 119 and all applicable statutes and treaties from prior U.S. provisional application Ser. No. 62/732,273, which was filed Sep. 17, 2018, and is incorporated by reference herein.

FIELD

A field of the invention is artificial muscles. Applications of the invention include any application in which actuators are used, and especially in applications where low weight, fine motion and high contractile work are required, including, for example, robotics and prosthetics.

BACKGROUND

Twisted and coiled fibers have been recently proposed as a new class of artificial muscles [1]. A torsional actuation from highly twisted fibers was demonstrated for the first time in 2011 [2]. Foroughi et al showed that a twisted carbon nanotube (CNT) yarn is able to provide a rotation of 250° $mm^{-1}$ when charged electro-chemically by immersion into an electrolyte. Subsequently, Lima et al discovered that tensile actuation can also be obtained from CNT yarns [3]. In this case, the yarn was overtwisted until a spontaneous formation of coils was observed, and when the ends are constrained from rotation but allowed to axially move, a tensile contraction around 7% was measured when the material was heated at incandescent temperatures. The addition of a volume expanding polymer, such as paraffin wax [3] or silicon rubber [4], was later adopted to allow the tensile actuation at lower temperatures. In particular, coiled CNTs yarns infiltrated by silicone rubber, showed a tensile actuation of 34% when electro-thermally actuated, and 50% when actuated by swelling [4]. Chemical swelling generally allows larger actuation strains because some polymers can swell up to 300%, albeit on the cost of actuation speed Although such performances are promising, the application of twisted and coiled CNT artificial muscles is limited by the high cost of fabrication involving aligned CNT yarns. In order to overcome this practical limit, polymeric fibers were proposed as twisted and coiled artificial muscles in 2014 [5]. These muscles include highly twisted low cost and common materials like sewing thread or fishing lines, and can provide tensile actuation higher than 30% when heated to 50° C. These muscles were actuated to physical changes in polymer molecular structure stimulated by heat.

There is significant interest in improving the performance of artificial muscles. Researchers seek new materials [6, 7] and applications [8-10] as the interest in artificial muscles grows.

The most common form of CNT muscle uses wax with the CNTs. The carbon nanotubes are employed for their strength and electrical properties, and the wax for a volumetric response. The CNTs are not easily formed into extended lengths, as the CNTs themselves have lengths limited to the nanoscale, generally being significantly less then 100 nm in length. A process to make CNT artificial muscle fibers forms a thin sheet of nanotubes. The sheet is sprayed with wax. The sheet is then twisted until it forms a yarn shape. The twisting of the sheets produces a relatively complex structure, with wrinkles, which is a poor replica of traditional elongate fiber yarns such as used in the textile industry. Wax is adopted because the wax expands greatly in response to heat.

The first theoretical model for the torsional and tensile actuation of twisted and coiled muscles respectively, was proposed by Haines et al [5]. In particular, the untwisting (and then the torsional stroke) is considered the consequence of the anisotropic volumetric expansion that the nylon fiber experiences during the heating process. Haines et al. proposed a geometric relation to relate the spontaneous untwisting to the change of the geometrical parameters of the fiber (i.e., the bias angle, the diameter, and the length). The spontaneous untwisting was also considered the cause of the tensile actuation of coiled fibers [5]. A simple geometric equation that relates the tensile stroke to the untwisting, the number of coils, and the length of the fiber, is derived based on Love's helix equation in his mathematical treatise on elasticity [11]. A single helix equivalent model was later developed by Aziz et al [12] to relate the kinematics of the untwist to the volume change caused by heating and demonstrate that the torsional stroke depends only on the inserted twist and is independent on fiber diameter. Lima et al [3, 4] described how coiled CNT yarns are able to provide large tensile strokes at lower temperatures if infiltrated with wax or silicone rubber, due to the higher volumetric thermal expansion coefficients of the matrix.

These models focus on the geometric expansion of a component in the artificial fibers, e.g., the wax. Artisans have generally focused on the expansive properties of the wax or other component that expands in response to heat generated by current flow in the CNTs. The present inventors have realized that other properties affect performance. Mere geometric/volumetric expansion can't be leveraged to optimize performance. The inventors have determined that a property of wax is a hinderance to performance, i.e., wax also loses viscosity with heating, and that new materials and fabrication methods are needed to improve performance. The manufacture of artificial muscles with CNTs is also expensive, and the length of a CNT artificial muscle is not easily made to a length that is preferable for many applications, such as robotics and prosthetics.

REFERENCES

[1] Haines C S, Li N, Spinks G M, Aliev A E, Di J T and Baughman R H 2016 New twist on artificial muscles Proc. Natl Acad. Sci. USA 113 11709-16
[2] Foroughi J et al 2011 Torsional carbon nanotube artificial muscles Science 334 494-7
[3] Lima M D et al 2012 Electrically, chemically, and photonically powered torsional and tensile actuation of hybrid carbon nanotube yarn muscles Science 338 928-32
[4] Lima M D, Hussain M W, Spinks G M, Naficy S, Hagenasr D, Bykova J S, Tolly D and Baughman R H 2015 Efficient, absorption-powered artificial muscles based on carbon nanotube hybrid yarns Small 11 3113-8
[5] Haines C S et al 2014 Artificial muscles from fishing line and sewing thread Science 343 868-72
[6] Mirvakili S M, Pazukha A, Sikkema W, Sinclair C W, Spinks G M, Baughman R H and Madden J D W 2013 Niobium nanowire yarns and their application as artificial muscles Adv. Funct. Mater. 23 4311-6
[7] Cheng H H, Hu Y, Zhao F, Dong Z L, Wang Y H, Chen N, Zhang Z P and Qu L T 2014 Moisture-activated torsional graphene-fiber motor Adv. Mater. 26 2909-13
[8] Lee J, Ko S, Kwon C H, Lima M D, Baughman R H and Kim S J 2016 Carbon nanotube yarn-based glucose sensing artificial muscle Small 12 2085-91

[9] Yip M C, Niemeyer G and Ieee 2015 High-performance robotic muscles from conductive nylon sewing thread IEEE Int. Conf. on Robotics and Automation (ICRA) (Seattle, Wash.) pp 2313-8
[10] Kim S H et al 2017 Harvesting electrical energy from carbon nanotube yarn twist Science 357 773-8
[11] Love A E H 1944 A treatise on the Mathematical Theory of Elasticity (New York: Dover)
[12] Aziz S, Foroughi J, Brown H R and Spinks G M 2016 Controlled and scalable torsional actuation of twisted nylon 6 fiber J. Polym. Sci. B 54 1278-86
[13] Thompson J M T and Champneys A R 1996 From helix to localized writhing in the torsional post-buckling of elastic rods Proc. R. Soc. A 452 117-38
[14] Timoshenko S P G J 1961 Theory of Elastic Stability (New York: McGraw-Hill)
[15] Bhat G 2017 Structure and Properties of High-Performance Fibers (Oxford: Woodhead) pp 63-5
[16] Choy C L, Chen F C and Young K 1981 Negative thermalexpansion in oriented crystalline polymers J. Polym. Sci. B 19 335-52
[17] Chun K Y et al 2014 Hybrid carbon nanotube yarn artificial muscle inspired by spider dragline silk Nat. Commun. 5 3322
[18] Naik N K and Madhavan V 2000 Twisted impregnated yarns: elastic properties J. Strain Anal. Eng. Des. 35 83-91
[19] Kim B, Park M, Kim Y S and Jeong U 2011 Thermal expansion and contraction of an elastomer stamp causes position-dependent polymer patterns in capillary force lithography ACS Appl. Mater. Interfaces 3 4695-702
[20] Zill D and Cullen C 1997 Differential Equations with Boundary-Value Problems (Pacific Grove, Calif.: Cengage)
[21] Liu M, Sun J R and Chen Q F 2009 Influences of heating temperature on mechanical properties of polydimethylsiloxane Sensors Actuators A 151 42-5
[22] Huber J E, Fleck N A and Ashby M F 1997 The selection of mechanical actuators based on performance indices Proc. R. Soc. A 453 2185-205
[23] Hopkins D A and Chamis C C 1988 A unique set of micromechanics equations for high-temperature metal matrix composites Testing Technology of Metal Matrix Composites (West Conshohocken, Pa.: ASTM) pp 159-75
[24] Johnston I D, McCluskey D K, Tan C K L and Tracey M C 2014 Mechanical characterization of bulk Sylgard 184 for microfluidics and microengineering J. Micromech. Microeng. 24
[25] Mounier D E A Evaluation of transverse elastic properties of fibers used in composite materials by laser resonant ultrasound spectroscopy Proc. Acoustic 2012 Conf. (Nantes)
[26] Krucinska I and Stypka T 1991 Direct measurement of the axial poisson ratio of single carbon-fibers Compos. Sci. Technol. 41 1-12.

SUMMARY OF THE INVENTION

A preferred embodiment is an elongate fiber artificial muscle that includes or consists of an elongate carbon or glass fiber and at least a partial coating of a polymer, and preferably a full shell coating to form a core-shell arrangement, that is volumetrically responsive to thermal changes or to moisture changes. Additional elongate fiber artificial muscles of the invention include a plurality of elongate carbon or glass fibers that are infiltrated between the fibers with a polymer that is volumetrically responsive to thermal changes or to moisture changes. In a fabrication method, the rheology (flow characteristic) of a polymer precursor is adjusted with solvent so it is less viscous. A fiber or plurality of fibers (pre-twisted or untwisted), such as a tow is dipped in the polymer precursor. The fiber or fibers is then pulled out of the polymer precursor and hung to allow polymer to distribute and then cured and can be twisted to coil prior to curing. A model is provided to fabricate elongate fiber artificial muscle with specific characteristics based upon a thermal or moisture expansion coefficient of the polymer, its elongation capability percentage before flaking or breaking, and its elastic modulus.

BRIEF DESCRIPTION OF THE DRAWINGS

FIG. 4A is an image of a prototype composite elongate fiber artificial muscle and FIG. 4B illustrates an experiment to test the prototype composite elongate fiber artificial muscle;

FIGS. 8A-8C are data plots and an image from load lift testing of a prototype composite elongate fiber artificial muscle.

DETAILED DESCRIPTION OF THE PREFERRED EMBODIMENTS

Figure 1:
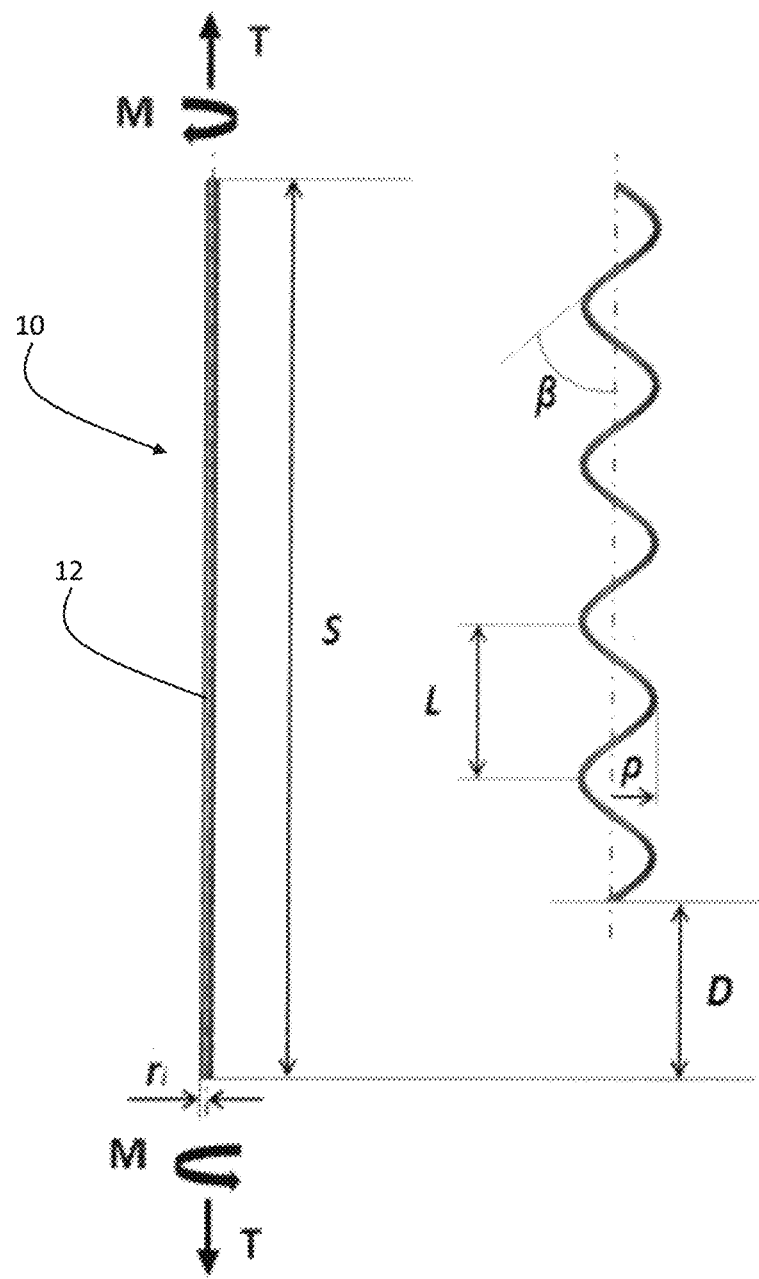
FIG. 1 is a schematic illustration of a preferred core-shell elongate fiber artificial muscle and its contraction.

A preferred elongate fiber artificial muscle includes or consists of an elongate carbon or glass fiber and at least a partial coating of a polymer, and preferably a full shell coating to form a core-shell arrangement, that is volumetrically responsive to thermal changes or to moisture changes. The volumetric response can be, for example, to heating, which can cause the polymer to volumetrically expand (increase in an axial and/or radial direction with respect to the artificial muscle). Similarly, cooling can cause the polymer to volumetrically contract (decrease in an axial and/or radial direction with respect to the artificial muscle). The corollary is true with respect to moisture responses that can be induced in certain polymers via increasing (wetting) or decreasing (drying) of the polymer. Preferred elongate fiber artificial muscles can therefore return to an initial (muscle relaxed) state after a stimulated response (muscle contraction) state. In one example, heating is induced through electrical stimulus applied to the elongate carbon fiber(s) and provides a contraction, and removal of the electrical stimulus allows cooling that allows the artificial muscle to relax. Over an operational range, the polymers can be cycled many times and retain the basic shape and structure of the elongate fiber artificial muscle.

Additional elongate fiber artificial muscles of the invention include a plurality of elongate carbon or glass fibers that are infiltrated between the fibers with a polymer that is volumetrically responsive to thermal changes or to moisture changes. The plurality of elongate fibers is preferably twisted together. In some variations, the elongate fibers each comprise a tow of individual fibers and the tows of fibers are then twisted together with infiltrated polymer. The polymer is selected for a plurality of characteristics, including its thermal or moisture expansion coefficient, its elongation capability percentage before flaking or breaking, and its elastic modulus. Preferred polymers substantially maintain or increase viscosity and shape during the expansion that is thermal or moisture induced.

Elongate fiber artificial muscles of the invention can also be formed into fabrics through traditional joining and weaving techniques, with or without regular (non-actuating) fibers of other materials. The elongate fiber artificial muscles of the invention more closely mimic textile fabrics than CNT based artificial muscles and can therefore be formed into a wider variety of lengths and shapes than CNT based artificial muscles. The carbon and glass fibers in the artificial muscles of the invention can advantageously have lengths, e.g., a meter, ten meter or a hundred meters, that are essentially infinite when compared to their diameters, which are, for example, 5 to 20 microns. Additionally, the elongate carbon and fiber artificial muscles of the invention have greater tensile strength than artificial muscles made with CNTs.

A preferred elongate fiber artificial muscle fabrication method employs an elongated carbon or glass fiber, and selects a polymer that volumetrically responsive to thermal changes or to moisture changes, then coats the carbon or glass fiber or infiltrates a plurality or tow of carbon or glass fibers. prepared uncured polymer. In preferred methods, the rheology (flow characteristic) of a polymer precursor is adjusted with solvent so it is less viscous. A fiber or plurality of fibers (pre-twisted or untwisted), such as a tow is dipped in the polymer precursor. The fiber or fibers is then pulled out of the polymer precursor and hung to allow polymer to distribute and cure. For an elongate fiber artificial muscle that consists of a single carbon or glass fiber, the polymer cures into a shell to form the elongate core-shell artificial muscle. A single fiber or plurality of fibers can also be twisted while being pulled, such as by a weight, and then cured. The twisting can continue prior to curing until a predetermined coiling occurs, and with an appropriately selected weight, the weight will move upward as the coiling occurs. The twisting can also be conducted before the polymer curing. The curing sets the final relaxed shape/geometry of the elongate fiber artificial muscle, and this shape/geometry is maintained over many cycles within operational limits of the polymer and elongate fibers.

Preferred embodiments of the invention will now be discussed with respect to the drawings and experiments used to demonstrate the invention. The drawings may include schematic representations, which will be understood by artisans in view of the general knowledge in the art and the description that follows. Features may be exaggerated in the drawings for emphasis, and features may not be to scale.

FIG. 1 shows a preferred embodiment elongate fiber artificial muscle 10 that includes or consists of an elongate carbon or glass fiber within shell coating 12 of a polymer that is volumetrically responsive to thermal changes or to moisture changes. A preferred polymer coating is an elastomer polymer, e.g., a silicon, such as Polydimethylsiloxane (PDMS), that exhibits a volumetric thermal response. Other polymers that are used in preferred embodiments include polymers that exhibit a volumetric moisture response, such as polyether polyols or stretchable and tough hydrogels. FIG. 1 shows the elongate fiber artificial muscle 10 in a straight and twisted configuration. The elongate fiber artificial muscle 10 can also comprise a plurality of fibers, with spaces between the fibers infiltrated with the polymer that is volumetrically responsive to thermal changes or to moisture changes. The fiber(s) in the elongate fiber artificial muscle are preferably carbon or glass with a diameter typically between 5 and 20 microns and much longer length, e.g., half or a full meter, ten meters, a hundred meters, etc. The fabrication of preferred elongate fiber artificial muscles will now be described with respect to design models that the inventors have developed for the selection of materials, including the polymer, and for the twisting of fibers during fabrication.

Prior theoretical models treat the geometry and kinematics of the actuation with no correlation between the performance, the loading conditions, and the mechanical properties of the material. Our preferred model focuses on the tensile actuation of coiled muscles providing a comprehensive theoretical model to explain the physical mechanism of their actuation and the limits of their performance. The model describes first the mechanics of coiling as related to the geometry and material properties of the fiber. The model goes beyond simple kinematics by relating the performance of the muscles not only to the geometric parameters of the coil, but also to the loading conditions and the thermo-electro-mechanical response of the materials. The starting point for the development of the model is the equilibrium of work and energy during the coiling of elastic rods, as proposed by Love [11], and revised by Thompson et al [13]. We have demonstrated via experiments and confirmed a model that we developed to show that the muscle contraction (i.e., the tensile actuation) is caused by the increase in the radius of the yarn, due to thermal expansion or solvent absorption. The increase of the radius causes an increment of the bending and the torsional stiffness. The elongated fiber artificial muscle equilibrium extension is offset by an increment of the coil angle, and the transition from the previous equilibrium position to the new equilibrium configuration of the stiffer coil leads to the contraction of the muscle.

The present model to enable fabrication of elongate fiber artificial muscles with specific desired properties was validated by experimental tests performed on preferred carbon fibers (CF)/Polydimethylsiloxane (PDMS) coiled muscles. The effect of the geometry of the twisted yarn is also considered, so that the methodology can be applied for the design and the optimization of any elongate fiber artificial coiled muscle. These muscles can be actuated by joule heating or moisture induced swelling, include induced by water such water content in atmospheric conditions. Example experimental elongate fiber artificial muscles support up to 60 MPa of mechanical stress and provide an actuation of 25% and a specific work of 758 J kg-1 when an input voltage of 1.64 V cm-1 is applied.

A model provided to design preferred elongate fiber artificial muscles characterizes the tensile actuation of coiled fiber reinforced artificial muscles as well as a preferred single elongate fiber core-shell muscle. The model is able to predict the final configuration of a spontaneously-formed coil obtained by overtwisting a straight elastic fiber, as well as estimate the tensile stroke of the coil when it is thermally or electro-thermally activated based upon the materials used in the fiber. The model relates the performances of the muscle to the loading conditions and the thermo-electrical-mechanical properties of the material, allowing the precise tailoring of the output tensile stroke and specific work.

Theoretical Model

When a straight and elastic fiber is highly twisted, a spontaneous formation of coils can be obtained if a critical condition of coiling instability is reached. The understanding of this phenomenon is crucial for the development of a mechanics model, able to explain the actuation mechanism of coiled artificial muscles. We use the nonlinear formulation of Love [11] to describe the coiling procedure of a highly twisted fiber. The starting configuration is represented by a straight fiber with length S and radius $r_i$, loaded at its ends by a twisting moment M, and a tensile load T, with the labels being applied to the preferred embodiment elongate fiber artificial muscle of FIG. 1. The fiber is assumed to be linearly elastic exhibiting no axial or shear deformability.

Under combined tension and moment, the straight fiber becomes unstable and form a spontaneous coil when the external loads M and T reach a critical value, Mc and Tc respectively, such that:

$$M_c^2 = 4BT_c, \quad (1)$$

where B is the bending stiffness of the fiber B=EI, where E is the Young modulus of the material and I the second moment of area. The critical condition expressed in equation (1) can be easily obtained by the linear eigenvalue analysis of Love [11] or Timoshenko [14].

$$L = \frac{2\pi\rho}{\tan\beta} \quad (2)$$

$$\rho = \frac{S\sin\beta}{2\pi N}, \quad (3)$$

where L is the coil pitch, $\rho$ its radius, $\beta$ is the coil angle, and N the number of coils formed spontaneously. The spontaneous contraction of the fiber, indicated as D in FIG. 1, is a geometric function of the coil angle and can be calculated as follows:

$$D = S(1 - \cos\beta). \quad (4)$$

To determine the geometry of the spontaneously formed coil, $\beta$ and N must be determined from the mechanics of coil formation. The total energy of the system can be written as:

$$V = V_T + V_M + V_B + V_C, \quad (5)$$

where $V_T$, $V_M$, $V_B$ and $V_C$ are the potential energy due to the tensile load T, the external moment M, the bending, and torsion respectively. All the energy terms listed in equation (5) can be written in relation to the external loads, the mechanical properties of the material, and the geometric parameters of the coils as follows:

$$V_T = TS(1 - \cos\beta) \quad (6)$$

$$V_M = -MS(\tau_i + \sin\beta/\rho) \quad (7)$$

$$V_B = \frac{1}{2} BS \sin^4\beta/\rho^2 \quad (8)$$

$$V_C = \frac{1}{2} CS[\tau_i + \sin\beta\cos\beta/\rho]^2, \quad (9)$$

where $\tau_i$ the internal twist, and C is the torsional stiffness, C=GJ, where G is the shear modulus of the material and J the polar second moment of area for a circular fiber. When the derivatives of the total energy with respect to the coil angle, the coil radius, and the internal twist, are set equal to zero, the equilibrium condition (muscle relaxed state)(i.e., after the formation of coils) can then be found. Under the minimum energy configuration, the following equations relating the fiber's material and geometry to the coiling, and as can be shown later the mechanics of its actuation, can be obtained:

$$\beta = \cos^{-1}\left[\frac{1}{B-C}\left(\frac{rBC}{\sqrt{BT}} - 2C\right) - 1\right] \quad (10)$$

$$N = \frac{S}{2\pi}\sqrt{\frac{T}{B}}. \quad (11)$$

The parameter r is the twist per unit length defined as total end rotation of the fiber in radians per unit length, calculated as follows:

$$r = \frac{2\pi n}{S}, \quad (12)$$

were n is the total number of turns applied during the twisting procedure. Equation (10) is very useful because it allows the design of the final geometry of the coil, starting from a straight fiber (with known dimensions and mechanical properties), by choosing the value of the applied tensile load T and number of turns n. We note from equation (11) that the number of coils N is a function of the tensile load T and the bending stiffness B only.

This simple equation can also be used to explain why a spontaneously coiled artificial muscle is able to provide a tensile actuation when it receives an input such as simple heating, Joule heating, or moisture (including solvent) absorption. The effect of all the different input typologies mentioned above is the volumetric expansion of the fiber. Such expansion can be anisotropic for some materials such as CNTs or carbon fibers, which experience a large expansion along the radius of the fiber and a small contraction along the longitudinal axis. This phenomenon is related to the anisotropy of the graphite crystallites, which exhibit different properties along the directions parallel and perpendicular to the basal plane [15]. Also some oriented crystalline polymers such as nylon show a similar anisotropy during volumetric expansion [16].

This anisotropic volumetric expansion plays an important role in the performance of the artificial muscle. In the model developed by Haines et al [5] it was considered the sole cause of the spontaneous untwisting, which was in turn proposed as the cause of the tensile actuation.

We explain the relation between the volumetric expansion, the untwisting, and the resulting actuation, in light of equation (10). The effect of the anisotropic volumetric expansion can be considered in equation (10) as an increment of the radius of the fiber from $r_i$ to $r_f$, while the length of the fiber S can be kept constant for the sake of simplicity (compared to the radius increase, the shortening of the fiber length can in fact be considered negligible for all the materials mentioned above, including fiber reinforced coiled muscles like carbon fiber-based or CNT-based muscles that were modeled by prior work including Haines et al. [5]). The radius increment causes then a significant increase of the bending and torsional stiffness B and C, as well as a variation of the coil angle $\beta$, from an initial configuration i to a final configuration f, as described by the following equations:

$$B_{i,f} = E\frac{\pi}{4} r_{i,f}^4 \quad (13)$$

$$C_{i,f} = G\frac{\pi}{2} r_{i,f}^4 \quad (14)$$

$$\beta_{i,f} = \cos^{-1}\left[\frac{1}{B_{i,f} - C_{i,f}}\left(\frac{rB_{i,f}C_{i,f}}{\sqrt{B_{i,f}T}} - 2C_{i,f}\right) - 1\right]. \quad (15)$$

Figure 2A:
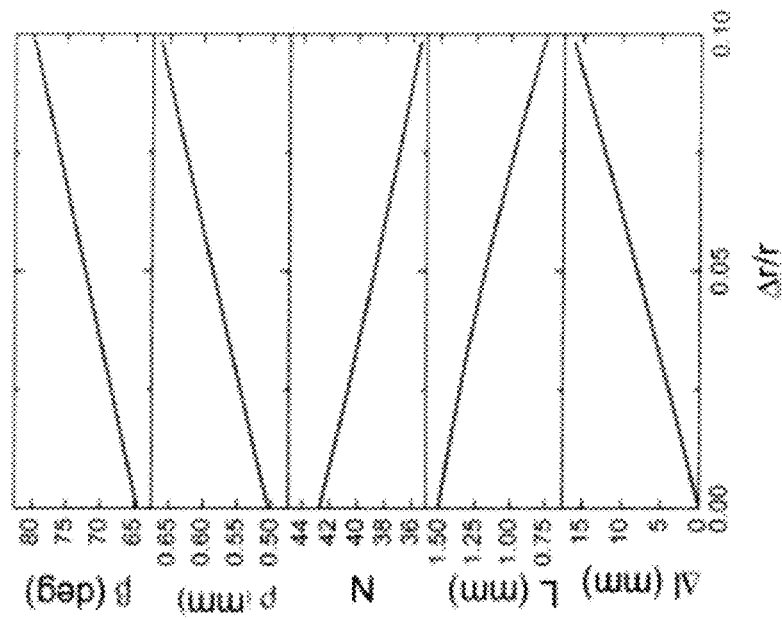
FIG. 2A is data regarding tensile contraction of a preferred twisted elongate fiber artificial muscle.
Figure 2B:
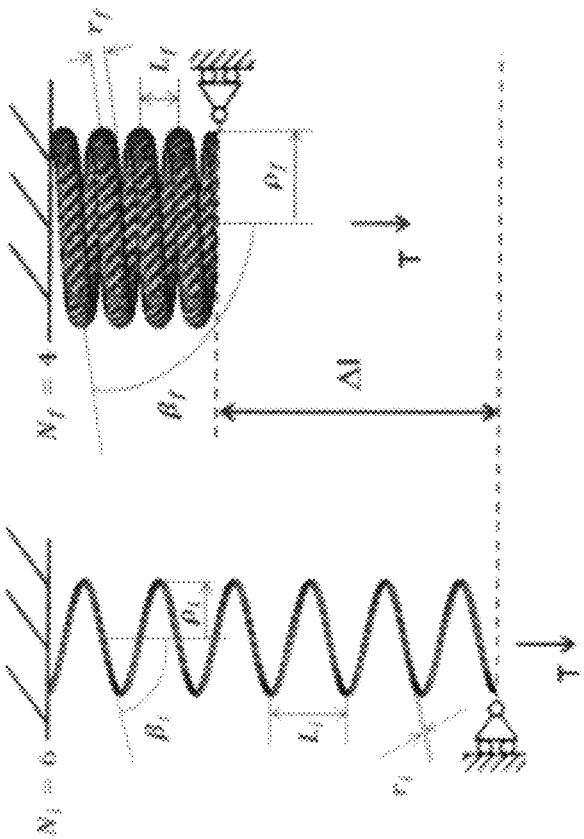
FIG. 2B illustrates the relaxed and contracted states and parameters that are used to model physical parameters of the twisted elongate fiber artificial muscle.

As a consequence, also the coil parameters N, L, and ρ will be subject to a variation (according to equations (11), (2), and (3), respectively), as shown in FIGS. 2A and 2B.

The result of the anisotropic volume expansion is then a 'new' stiffer coil, characterized by a different equilibrium position. The direct consequence of this new equilibrium condition is the shortening of the coil by a displacement Δl, leading to tensile actuation. The tensile stroke, that corresponds to the displacement of the bottom end, can be calculated by simple geometrical considerations as follows:

$$\Delta l = S(\cos \beta_i - \cos \beta_f). \quad (16)$$

Equations (13)(16) can then be used to predict the tensile actuation of any coiled fiber that experiences an anisotropic volume expansion. In particular, the initial geometry of the coil can be controlled using equation (15), by knowing the mechanical properties of the material (i.e., E, G), the initial dimensions (i.e., $r_i$, S), and controlling the external loads (i.e., T and n). A suitable input stimulus (thermal, electrical, or by swelling) can then be chosen in order to provide a radius increment able to produce a desired output displacement. Equation (16) provides for calculation of the output contraction related to the coil angle change. With (15) on can calculate the coil angle change according to the geometry of the fiber (radius, initial straight length), the mechanical properties of the materials used ($E_x$, $G_{yz}$) and the applied external load (both attached weight and twisting moment).

Anisotropy of the Fiber Reinforced Muscles

The model provided so far is useful to characterize the tensile actuation of coiled artificial muscles. However, it models material with isotropic mechanical properties. In equations (13) and (14), only a single value for the Young's modulus E and the shear modulus G is considered.

We have realized that other material properties play an important role, and that design and optimization should consider the thermal or moisture expansion coefficient of the polymer, its elongation capability percentage before flaking or breaking, and its elastic modulus. Our model provides for the design, fabrication and optimization of elongate fiber artificial muscles of the invention with consideration of such factors.

Figures 3A, 3B, 3C:
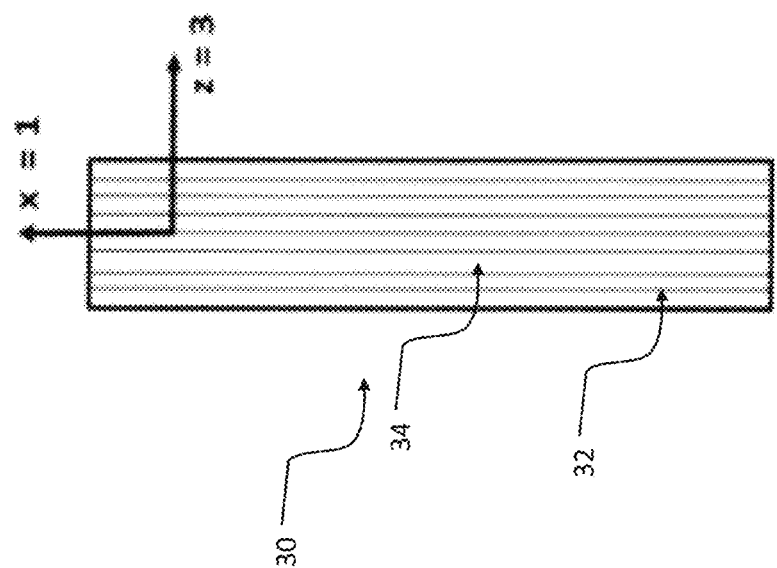
FIGS. 3A to 3C illustrated a preferred composite elongate fiber artificial muscle having long fibers in a polymer matrix along with on-axis reference system and global position reference system of parameters.

We consider the generic case of a composite elongate fiber artificial muscle 30 of the invention that includes a plurality of elongate glass or carbon fibers 32 that are infiltrated with a polymer 34 that has a thermal or moisture volumetric response, as shown in FIGS. 3A-3C, which respectively show non-twisted, partially twisted and an image of a fully twisted elongate fiber artificial muscle 30 of the invention in the form of a yarn. The following description of the theoretical model will refer to the composite yarn that is shown in FIG. 3C.

In particular, the composite elongate fiber artificial muscle of FIGS. 3A-3C characterized by long fibers in a matrix that has been infiltrated with polymer having a thermal or moisture volumetric response, and then is twisted to produce the yarn of FIG. 3C. Before twisting insertion, the on-axis reference system 1, 2, 3 coincides with the global system x, y, z, as shown in FIG. 3A. After the twisting procedure, an angle α is generated between the fibers (axis 1) and the x axis, as shown in FIG. 3B. Such angle coincides with the external twist angle of the fibers yarn and is defined positive when is measured in a counter-clock-wise direction from the axis 1 to the axis x (for such reason the twist angle in FIG. 3C has been indicated as—α). If during the coiling procedure the tensile load T is applied along the x direction and the external moment M around the x axis, equations (13) and (14) are modified as follows:

$$B_{i,f} = E_x \frac{\pi}{4} r_{i,f}^4 \quad (17)$$

$$C_{i,f} = G_{yz} \frac{\pi}{2} r_{i,f}^4. \quad (18)$$

$E_x$ in this case is the relevant modulus as the resistance to bending B of the muscle is the resistance to extension in the x-direction above and below the neutral axis of the coiled muscles. The Naik et al model [18] is used to calculate $E_x$ and $G_{yz}$ from the known mechanical properties of the polymer matrix material and the elongate fibers.

Prototype elongate fiber artificial muscle fabrication and experimental setup.

Experiments validated out model that is explained with respect to FIGS. 3A-3C. In addition, a low-cost and relatively simple fabrication process was developed and will be explained. Details of the experiments are discussed next.

Commercial Thornel-T300 PAN-based carbon fibers (CF), supplied with 1% UC.309 epoxy-compatible sizing, were used. One CF tow (containing 24500 fibers) is first dipped into uncured Sylgard 184 PDMS, diluted with hexane (2:1 by weight). Hexane serves to decrease the viscosity of the PDMS and obtain a more homogeneous distribution of the PDMS inside the CF tow. At the end of the dipping stage, the tow is twisted by using a simple drill. The composite yarn with twisted carbon fibers (with both ends tethered) is then placed in the oven at 50° C. for 24 h in order to cure the PDMS.

The twisting procedure before the curing of the PDMS also serves to eliminate excessive liquid PDMS and obtain an initial straight composite yarn with a homogeneous shape and a constant radius as shown in FIG. 3C. In particular, 240 turns m$^{-1}$ were applied during the pre-twisting procedure, which led to a composite yarn with a PDMS content of ~40% wt and radius of ~200 μm. During twisting, the PDMS redistributed filling the gaps between the fibers and the excess deposits on the outside of the composite yarn. One can observe that the curing of the PDMS froze the twisting of the carbon fibers at a certain angle α. The measurement of such angle is important for the calculation of the mechanical properties of the composite and twisting to obtain a certain (predetermined) angle α provides a design option that can assist in the fabrication of elongate fiber artificial muscles of the invention.

When the PDMS is cured, the straight composite yarn was then highly twisted until it was fully coiled. FIG. 4A is an image of an example of fully coiled elongate fiber CF/PDMS artificial muscle, and FIG. 4B shows the experimental set-up with used to actuate the FIG. 4A elongate fiber CF/PDMS artificial muscle.

In FIG. 4B, a DC input voltage was applied at the coil ends in order to induce the heating of the composite yarn and the radius increase, causing of the tensile actuation. The tensile stroke was captured by a movie camera and the displacement was measured by the analysis of movie frames. The top end of the coil was fixed, while a weight was attached to the bottom end in order to apply a targeted tensile load. A horizontal rigid rod was attached to the weight and place in contact with two vertical rails in order to avoid its rotation. A ruler with a 0.5 mm resolution was attached to one of the vertical surfaces to facilitate the displacement measurements.

Experimental Validation for Electro-Thermally Actuated Muscles

The ability of our new model to predict the tensile actuation of fiber reinforced coiled muscles was tested on the produced elongate fiber CF/PDMS composite yarn artificial muscles. A straight yarn with a radius $r_i$=192 μm and an initial length S=16.5 cm is highly twisted in order to induce the spontaneous coiling. One hundred and fifty turns n=150 and a tensile load T=0.44 N are applied. Under such loading conditions, a contraction of the coil equal to 9.8 cm and a total number of coils N=41 are measured and they are in perfect agreement with the theoretical predictions of D=9.7 cm and N=39.24 obtained from equations (4) and (11) respectively), confirming the capability of our model to evaluate the final configuration of the composite yarn at the end of the coiling procedure, and to guide in the design and fabrication of additional elongate fiber artificial muscles consistent with the present invention.

Our model was also verified to predict the tensile actuation of the experimental coiled muscle. A DC input voltage is applied to the extremities of the coil to induce an increment of the radius of the yarn by Joule heating and relate this increment to the output coil contraction. This procedure allows to experimentally obtain the plot $\Delta l$-($\Delta r/r$) of FIG. 2A and then a direct comparison with the theoretical predictions, and FIG. 2B illustrates parameters associated with the relaxed and contracted state.

Figure 5A:
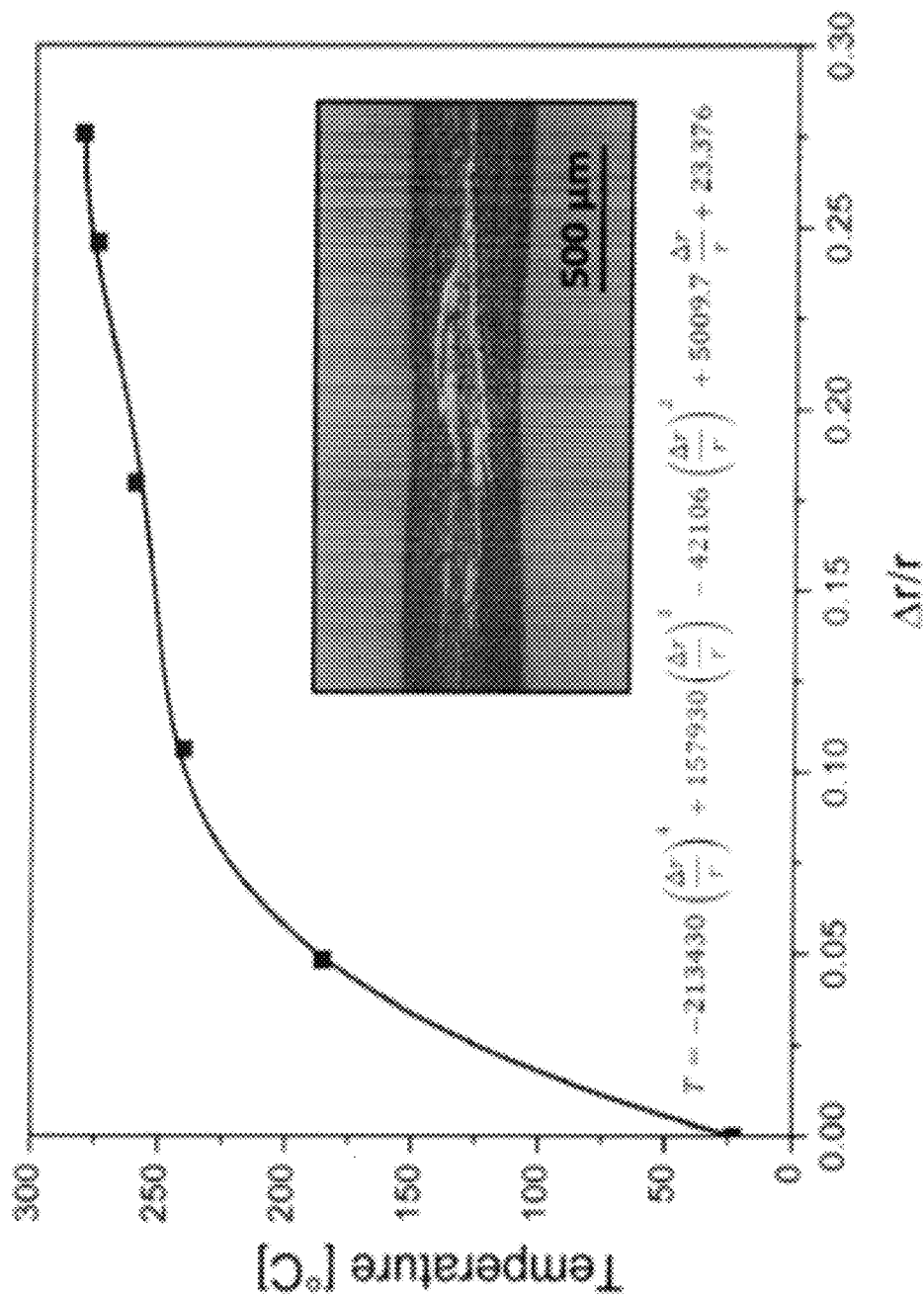
FIGS. 5A and 5B are experimental data concerning a prototype composite elongate fiber artificial muscle.

An in-situ measurement of the radius increment during the tensile actuation process is extremely challenging, due to the untwisting and the translation experienced by the muscle, combined to the small entity of the increment itself. On the other hand, using an infrared camera, the temperature of the coil can be easily measured during the actuation. We combine this in-situ temperature measurement with an ex-situ measurement of the radius increment as function of heating for a twisted fiber without coiling. In the latter experiment, a straight yarn is placed under the optical microscope, and its expansion under Joule heating is recorded with a movie camera in order to measure the radius increment from the analysis of movie frames. The temperature is measured by a thermocouple in contact with the yarn. The correlation between the temperature and the radius increment is then obtained and it is shown in FIG. 5A. The slope of the initial linear region in the plot is equal to $3\times10^{-4}$ °C.$^{-1}$, that corresponds to the linear thermal expansion coefficient CTE of the Sylgard 184 [19].

Next, the temperature is measured during the actuation of the coiled muscle and the experimental $\Delta r/r$ value is calculated from the plot of FIG. 5A. In particular, the temperature during the tensile actuation of the coil is recorded by a thermal camera (inset in FIG. 5B).

The $\Delta r/r$ experimental values are then correlated to the values of the displacement $\Delta l$ measured during the electrical actuation (through the analysis of movie frames. A near perfect agreement between the experimental results and the theoretical prediction can be observed. The theoretical plot was obtained from equations (15) to (18) by increasing the radius of the yarn. The geometrical parameters and loading conditions listed above (i.e., $r_i$=192 μm; S=16.5; n=150; T=0.44 N) are used in the calculations. The calculation of the mechanical properties $E_x$ and $G_{yz}$ is described below (the value of the twist angle α and the CF volumetric fraction $v_f$, needed or the mechanical properties evaluation, were measured by optical images and SEM analysis respectively.

Figure 5B:
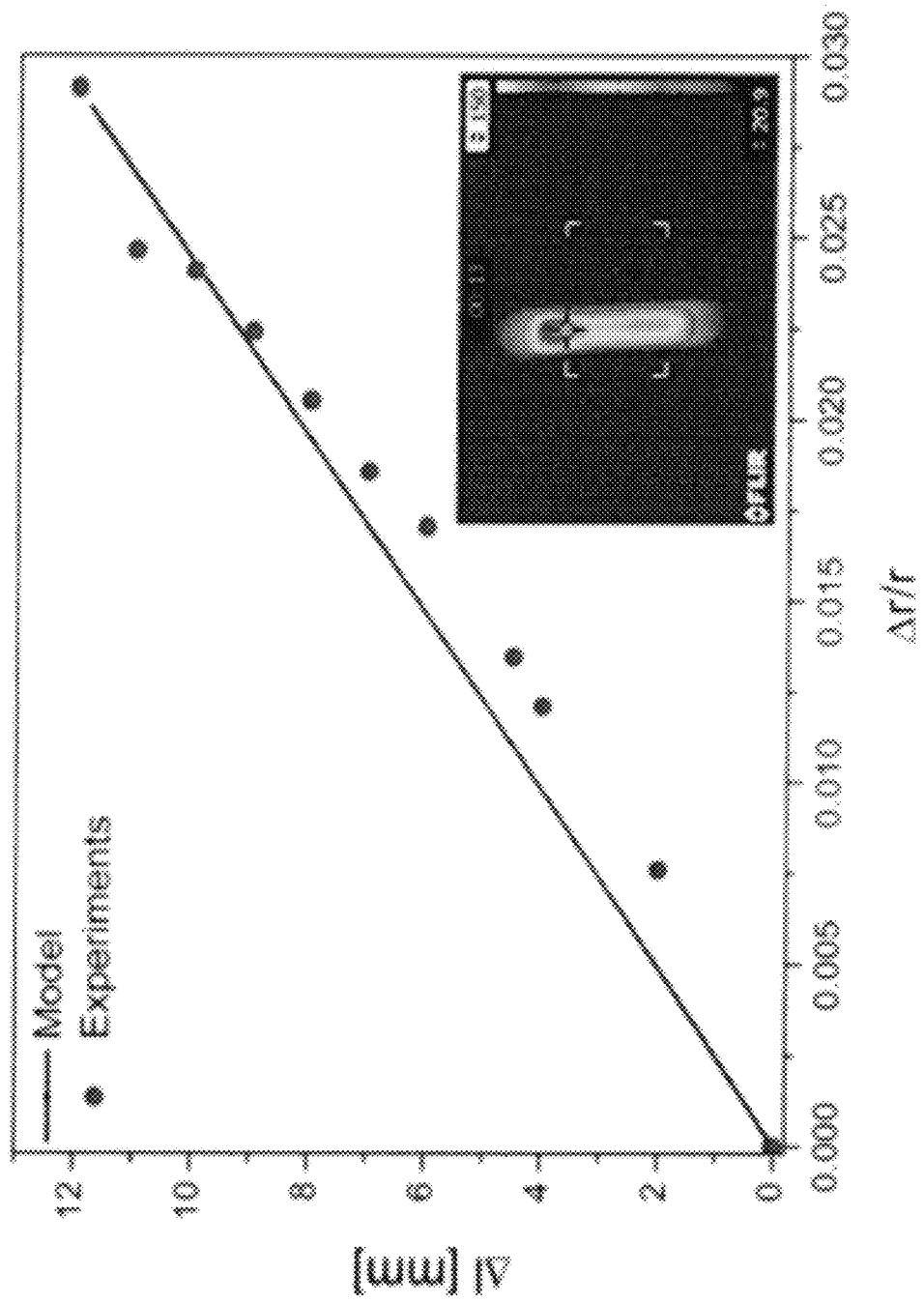

The experimental data of FIG. 5B corresponds to electrical actuation performed using a DC input voltage of 7.5 V, for 9 s. A temperature of 130° C. is measured by the thermal camera after 9 s (inset in FIG. 5B).

The theoretical prediction of the tensile displacement can be further generalized if we consider the simple equation that rules the Joule heating phenomenon[20]:

$$T(t) = e^{-pt}\left(\frac{C}{p}e^{pt} + \left(T_{amb} - \frac{C}{p}\right)\right) \quad (19)$$

were:

$$p = \frac{hA_s}{mc_p} \quad (20)$$

$$C = \left(\frac{V(t)^2}{R} + hA_s T_{amb}\right)\left(\frac{1}{mc_p}\right). \quad (21)$$

T is the instantaneous temperature at time t when a voltage V is applied on a yarn of mass m, electrical resistance R, section $A_s$, and specific heat $c_p$. h is the convection coefficient between the yarn and the surrounding air at temperature Tamb that in conditions of free convection is equal to 1 Wm$^{-2}$° C.$^{-1}$. The product m $c_p$ in equation (20) corresponds to the properties of the composite material where m $c_p$=$m_{matrix} c_{pmatrix}$+$m_{fiber} c_{pfiber}$.

Equation (19) can be used to predict the temperature reached by the coil if an input voltage V is applied for a time t, with no need for temperature measurements by a thermal camera during the coil actuation. In particular, according to equation (19), and using the geometrical and thermal properties of the tested coil (measured resistance R=40Ω, $A_s$=π (192 μm)2, $m_{PDMS}$=0.041 g, $c_{pPDMS}$=1 Jg-1° C.-1, $m_{CF}$=0.046 g, $c_{pCF}$=1.46 J g$^{-1}$° C.$^{-1}$), a value of V equal to 7.1 V has to be used for 9 s to reach a temperature T (9)=130° C. Such value is extremely close to the used value of 7.5 V (the used voltage is slightly higher because equation (19) does not consider the heat loss due to the electrical wires used for the actuation), confirming the suit-ability of equation (19).

Figure 6:
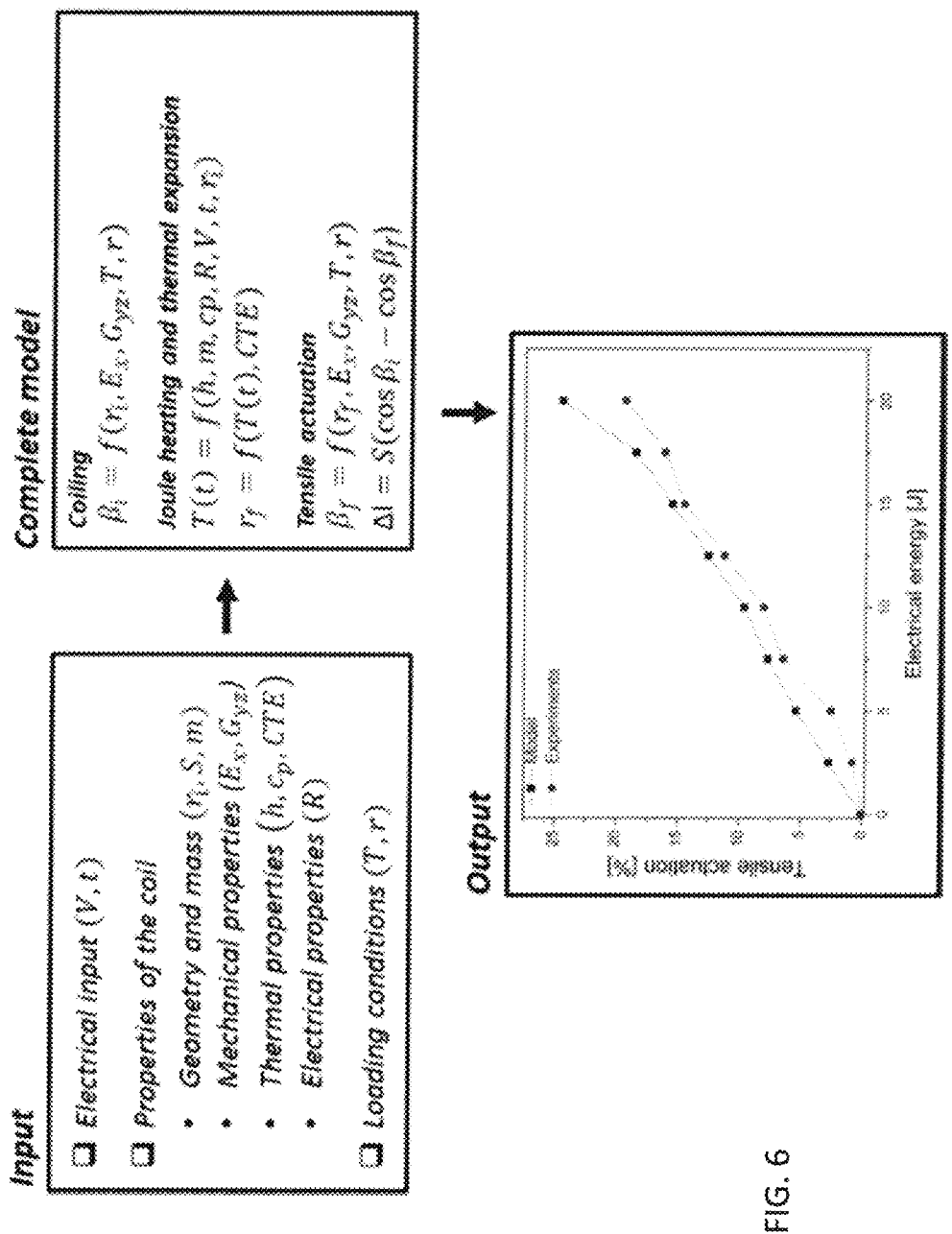
FIG. 6 compares modeled and measured data with the parameters used to model.

Therefore, using equations (15)(21), the tensile performances of an electrically activated fiber-reinforced coiled muscle can be directly predicted from the geometrical, mechanical, thermal, and electrical properties of the composite material, according to the applied loading conditions. FIG. 6 shows how the comprehensive model proposed in the present work led to the evaluation of the tensile stroke of a coiled muscle actuated with an input voltage of 10 V for 8 s.

Tailoring the Performance of Elongate Fiber Artificial Coiled Muscles

Our model allows the tailoring of the muscle size and performance. In particular, the tensile actuation of a coiled muscle composed by a yarn of fibers and a volumetrically responsive polymer (like the CF/PDMS muscles analyzed above) can be limited by two factors: the limited expansion of the polymer material, or the coil-coil contact. The first limit is strictly related to the properties of the polymer material that, above its degradation temperature, it is not able to provide an additional volume expansion. This is why muscles actuated by swelling have higher actuation strains, as they are able to swell significantly more than heat-induced expansion without degradation. On the other hand, the coil-coil contact is a geometrical limit: when adjacent coils come into contact, the muscle can no longer contract, even if the polymer material is below its degradation temperature and is able to cause an additional increment of the radius of the fiber. The interplay between these two limits and their effect on the muscle's performance can be easily analyzed using our model.

PDMS usually starts to degrade at temperatures higher than 200° C. [21]. We observed clear smoke associated with degradation of the used Sylgard 184 for temperatures higher than 230° C., as measured by the infrared camera. Since the expansion of the PDMS can no longer be exploited after its evaporation, the temperature of 230° C. was considered the limit working temperature of the produced CF/PDMS muscles. From the plot in FIG. 5A this temperature corresponds to a radius increment $\Delta r/r$ equal to 0.1. Using this value of the radius increments, the theoretical plots in FIGS. 7A-7D are obtained by equations (15)(18).

Figure 7A:
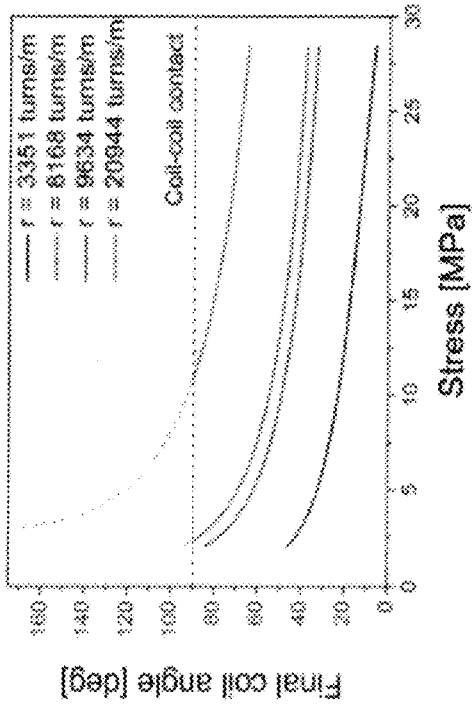
FIGS. 7A-7D are data plots characterizing a prototype composite elongate fiber artificial muscle.
Figure 7B:
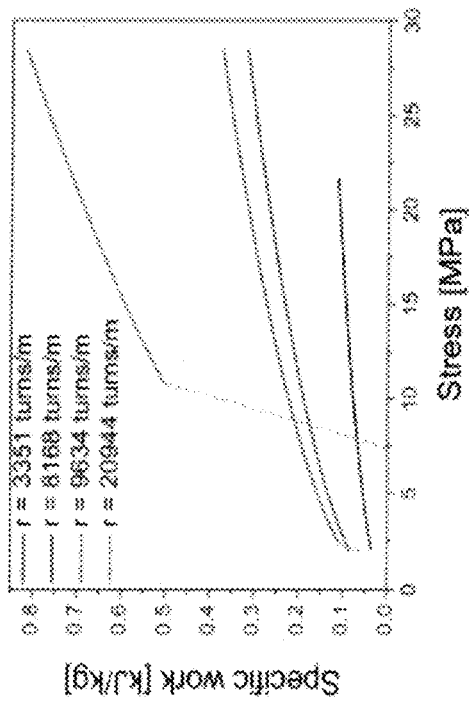

FIGS. 7A & 7B show how the initial coil angle $\beta_i$ and the final coil angle $\beta_f$ vary for different values of tensile stress and inserted twist. With a constant twist r (and then a constant number of turns, n), the value of the initial coil angle decreases with increasing values of the applied tensile stress.

Figure 7C:
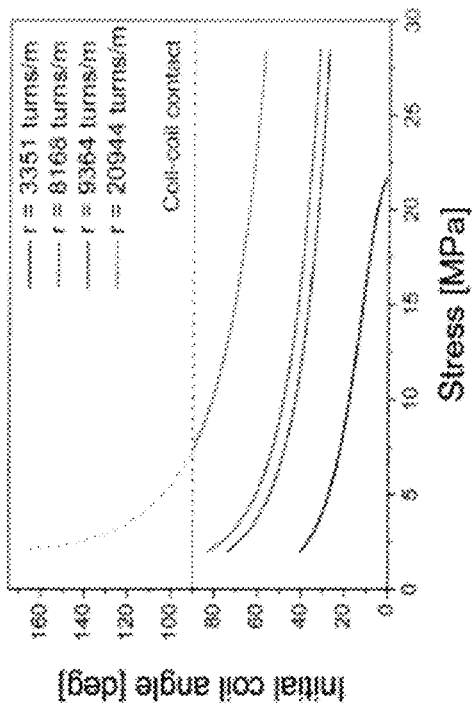

When the applied load is larger, the coil is more stretched, and the coil angle is smaller. At high stress and small number of turns, βi reaches the zero value (solid curves in FIG. 7A), corresponding to a straight yarn configuration. The increment in the number of turns causes instead an increase in the initial coil angle, and, with a very high number of turns and a small applied stress, the other limit configuration of the coil-coil contact, with a coil angle equal to 90° (dashed curves) can be reached. Similar considerations can be deduced for the final angle βf related to the condition of maximum expansion of the PDMS. The effect of the variation of the initial and final coil angles on the performance of the muscles can be observed in FIGS. 7C and 7D. FIG. 7C clearly shows that the maximum tensile actuation of the stress/turns configurations represented (i.e., 17% and 42% respectively) is only limited by the exploitable expansion of the PDMS, whereas the coil-coil contact limits the actuation in the other two cases. It is worth noting that the maximum tensile actuation obtained at the coil-coil contact configuration is constant for different stress/turns combinations. In particular, it is equal to 46% for a CNTs/PDMS yarn with the following properties: $r_i$=183 μm, S=15 cm, Ex=920 MPa, $G_{yz}$=23 MPa. FIG. 7C also demonstrates how the model is able to indicate which value of the tensile load has to be used to reach a desired tensile actuation when a certain number of turns r is applied. This guides the choice of the muscle diameter and length.

The results of FIG. 7 can be further generalized and a single master curve, to describe the universal performance of elongate fiber artificial muscles from the same material. FIGS. 8A and 8B show how the curves FIGS. 7C and 7D, related to different number of turns, can collapse in a single curve if the stress/$r^2$ ratio (where r is the twist per unit length) is considered instead of the simple stress along the horizontal axis. More specifically, the trend of the specific work can be generalized considering a reference number of turns $r_0$, as shown in FIG. 8B.

FIGS. 8A and 8B show experimental results for two different elongate fiber artificial muscles are also shown and good agreement with the theoretical prediction can be observed. We next clarify for the understanding of artisans, how the maximum value obtained for the experimental tensile actuation. Both the tested muscles were coiled using an inserted twist r=8168 turns m$^{-1}$. According to the theoretical predictions of the in FIG. 7C, a maximum tensile actuation bigger than 40% (obtained in conditions close to the coil coil contact) is expected when a stress of 2 MPa is applied to a muscle with an inserted twist of 8168 turns m$^{-1}$. However, the maximum tensile actuation measured for these muscles never exceeded a value of 25% (as shown in FIG. 8A. This discrepancy between the theoretical and the experimental maximum tensile actuation results from the fact that equation (16) assumes that the coiled muscle is modeled as an elastic line with zero thickness. Due to the thickness (i.e. the radius) of the yarn, the real coil-coil contact is reached for coil angles lower than 90°, and, as a consequence, the real maximum tensile actuation is lower than the maximum theoretical one.

Figure 7D:
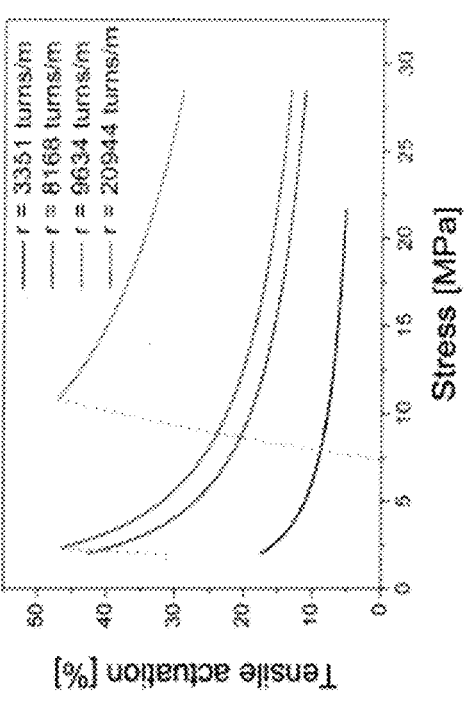

FIGS. 7C and 7D, the fabricated CF/PDMS coiled muscles are able to provide a maximum tensile actuation up to 25% and a maximum specific work of 0.758 kJ kg$^{-1}$ (this value can be calculated from FIG. 8(b) considering that the experimental data refer to an inserted twist r=8168 turns m$^{-1}$). Moreover, they are able to lift more than 12 600 times their own weight and support up to 60 MPa of mechanical stress.

The value of tensile actuation is higher (~25% for the present elongate fibers) than the maximum value obtained for electrically actuated coiled Fermat CNT yarns infiltrated with wax (~3%) [3], and comparable to the tensile strokes of thermally actuated coiled nylon fibers [5] and electrically actuated CNTS yarns infiltrated by silicone rubber (~30%) [4]. We note that the performances of CNT muscles in the works by Lima et al [3, 4] were optimized using dynamic electrical actuation which could enable higher instantaneous expansion, as well-as dynamic inertial effects in the load. The CF elongate fiber/PDMS artificial muscles studied in the present experiments were tested by using a DC electrical input. Dynamic electrical actuation is expected to improve performance of the present CF elongate fiber/PDMS artificial muscles.

Furthermore, a tensile actuation up to 58% is recorded for the CF elongate fiber/PDMS artificial muscles when very low tensile loads and high number of turns are applied. Under such loading conditions, tertiary coiling is encountered, and the model is not valid. The starting configuration of the muscle is very close to the coil-coil contact (as shown in FIG. 7A) and when the coils contact each other, the fiber continues to increase its radius until the muscle folds back on itself due to the low applied stress. Similar results, with tensile strokes up to 34% were also measured when the CF elongate fiber/PDMS artificial muscles were actuated by swelling. The PDMS swelling was induced by delivering liquid hexane on the coiled muscle. The tensile actuation is larger than the Joule heating case due to the larger local expansion caused by swelling.

The maximum specific work of 0.758 kJ kg-1 is very close to the maximum value of 0.836 kJ kg$^{-1}$ obtained for hybrid coiled CNTS yarns [3]. Compared to the CNT-based artificial muscles, important advantages of the CF elongate fiber/PDMS artificial muscles include the simple production process and the readily available constituents. A coiled CF elongate fiber/PDMS artificial muscles can be produced from commercial CF without using advanced equipment and with low fabrication costs. Producing larger muscles is also straightforward, while being extremely challenging for both CNT coils (due to the production process and the high fabrication cost) and nylon fibers (due to the difficulty in con-trolling the degree of orientation of the polymeric chains, responsible for the anisotropic expansion, during the drawing process [5]). As an example, we demonstrated a CF elongate fiber/PDMS artificial muscles with a radius of 0.4 mm able to lift a half gallon of water more than 1 inch (as shown in FIG. 8C), with only 0.172 V cm$^{-1}$. An efficiency of 1% (calculated as the ratio between the output mechanical energy and the input electrical energy, according to the following equation:

$$\eta = \frac{T\Delta l}{VI_c t},$$

where T is the applied tensile load, $\Delta l$ the obtained displacement, V the applied voltage, Ic the applied current, and t the time) is obtained, which is higher than that one obtained for CNT yarns (0.55%) [3], and close to commercially used shape memory metals (1%-2%) [22].

The thicker coil is tested for different stress values and results are shown in FIGS. 8A and 8B (star symbols). The trend of the tensile actuation and the specific work for the bigger muscle is the same of that one related to a fiber with a smaller radius (pentagon symbols), coiled using the same inserted twist r=8168 turns m−1. This result confirms that for a certain number of turns, the tensile performances of coiled muscles are scale invariant, as observed elsewhere [5, 12].

The master curves of FIGS. 8A and 8B are a powerful tool for the design CF elongate fiber/polymer artificial muscles since they are able to describe their universal performance as a direct consequence of the mechanical properties and the maximum expansion of the volumetric responsive polymer material, with no dependence on fiber dimensions and number of turns.

Elastic Properties of Twisted CF Elongate Fiber/PDMS Artificial Muscles

An analytical model to predict the off-axis elastic properties of a composite characterized by multi-level twisted filaments embedded into a matrix (i.e., the configuration of the straight fiber before coiling shown in FIG. 3C) was described by Naik et al [18]. The principal equations that can be used to relate the off-axis mechanical properties of a twisted impregnated yarn are next likened to the elastic properties of the present elongated fiber artificial muscle.

The following notation is considered:

$S_{ij}$, with i, j=1, . . . 6, are the terms of the compliance matrix of the impregnated straight filament (i.e., a straight fiber embedded into the matrix);

$S^a_{ij}$, with i, j=1, . . . 6 are the terms of the compliance matrix of the twisted impregnated filament (i.e., a twisted fiber embedded into the matrix);

$S^y_{ij}$, with i, j=1, . . . 6, are the terms of the compliance matrix of the twisted impregnated yarn (i.e., a yarn of twisted fibers embedded into the matrix);

The compliance matrix of the impregnated straight filament [S], is the compliance matrix of an orthotropic transversely isotropic material, characterized by five independent elastic constants $E_1$, $E_2$, $v_{12}$, $v_{23}$, $G_{12}$:

$$[S] = \begin{bmatrix} \frac{1}{E_1} & \frac{-v_{12}}{E_2} & \frac{-v_{12}}{E_2} & 0 & 0 & 0 \\ \frac{-v_{12}}{E_1} & \frac{1}{E_2} & \frac{-v_{23}}{E_2} & 0 & 0 & 0 \\ \frac{-v_{12}}{E_1} & \frac{-v_{23}}{E_2} & \frac{1}{E_2} & 0 & 0 & 0 \\ 0 & 0 & 0 & \frac{2(1+v_{23})}{E_2} & 0 & 0 \\ 0 & 0 & 0 & 0 & \frac{1}{G_{12}} & 0 \\ 0 & 0 & 0 & 0 & 0 & \frac{1}{G_{12}} \end{bmatrix}. \quad (A1)$$

The five independent elastic constants can be calculated from the mechanical properties of the composite constituents by means of well-known models, such as the rule of mixtures (equations (A2)-(A4)) or Hopkins and Chamis model [23](equations (A5) and (A6)):

$$E_1 = E_{f1}v_f + E_m v_m \quad (A2)$$

$$v_{12} = v_{f12}v_f + v_m v_m \quad (A3)$$

$$v_{23} = v_{f23}v_f + v_m v_m \quad (A4)$$

$$E_2 = E_m\left[(1-\sqrt{v_f}) + \frac{\sqrt{v_f}}{1-\sqrt{v_f}\left(1-\frac{E_m}{E_{f2}}\right)}\right] \quad (A5)$$

$$G_{12} = G_m\left[(1-\sqrt{v_f}) + \frac{\sqrt{v_f}}{1-\sqrt{v_f}\left(1-\frac{G_m}{G_{f12}}\right)}\right] \quad (A6)$$

were the subscript m refers to the matrix properties and f to the fiber properties, E is the Young modulus, G the shear modulus, v the Poisson ratio and v the volumetric fraction.

Concerning the CF/PDMS composite analyzed above, the volumetric fraction of the carbon fibers of has been measured by means of SEM analysis on the cross section of the straight fiber before the coiling procedure (shown in FIG. 3C). The elastic properties of the elongate CF/PDMS artificial muscle used for the calculations were the following values: $E_m$=3 MPa, Gm=1 MPa, vm=0.5, $E_{f1}$=230 GPa, $E_{f2}$=16 GPa, $G_{f1}2$=14 GPa, $v_{12}$=0.2, $v_{f23}$=0.31.

The terms of the compliance matrix of the twisted impregnated filament $S^a_{ij}$ can be related to the terms of the compliance matrix of the impregnated straight filament $S_{ij}$ (listed in equation (A1)) as follows [18]:

$S_{11}^a = S_{11}\cos^4\alpha + S_{22}\sin^4\alpha + (2S_{12}+S_{66})\cos^2\alpha\sin^2\alpha$ $S_{12}^a = \frac{1}{2}[(S_{11}+S_{22}-S_{66})\cos^2\alpha\sin^2\alpha + S_{12}\times(\cos^4\alpha+\sin^4\alpha+\cos^2\alpha)+S_{23}\sin^2\alpha]$ $S_{13}^a = S_{12}^a$ $S_{22}^a = \frac{1}{8}[3S_{11}\sin^4\alpha + (2S_{12}+S_{66})\times(1+3\cos^2\alpha)\sin^2\alpha + 3S_{22}(1+\cos^4\alpha)+(2S_{23}+S_{44})\cos^2\alpha]$ $S_{33}^a = S_{22}^a$ $S_{23}^a = \frac{1}{8}[S_{11}\sin^4\alpha + 2[S_{12}\cos^2\alpha\sin^2\alpha + S_{22}\times(1+\cos^4\alpha) - S_{44}\cos^2\alpha - S_{66}\sin^4\alpha + 6(S_{12}\sin^2\alpha + S_{23}\cos^2\alpha)]$ $S_{44}^a = \frac{1}{2}[(S_{11}-2S_{12})\sin^4\alpha + S_{22}(1+\cos^4\alpha)+(S_{44}-2S_{23})\cos^2\alpha + S_{66}\sin^2\alpha(1+\cos^2\alpha)]$ $$S_{55}{}^a = 2(S_{11} - 2S_{12} + S_{22})\cos^2\alpha \sin^2\alpha + \tfrac{1}{2}(S_{66}[\cos^2(2\alpha) + \cos^2\alpha] + S_{44}\sin^2\alpha)$$

$$S_{66}{}^a = S_{55}{}^a \tag{A7}$$

were α is the twist angle that can be optically measured.

Knowing the matrix [Sa], the terms of the compliance matrix of the twisted impregnated yarn $S^y{}_{ij}$ can be obtained by the following relationships [18]:

$$S_{11}{}^y = S_{11}{}^a I_1 + S_{22}{}^a I_2 + (2S_{11}{}^a + S_{66}{}^a)I_4$$

$$S_{12}{}^y = \tfrac{1}{2}[(S_{11}{}^a + S_{22}{}^a - S_{66}{}^a)I_4 + S_{12}{}^a \times (I_1 + I_2 + I_3) + S_{23}{}^a I_5]$$

$$S_{13}{}^y = S_{12}{}^y$$

$$S_{22}{}^y = \tfrac{1}{8}[3S_{11}{}^a I_2 + (2S_{12}{}^a + S_{66}{}^a)(I_5 + 3I_4) + 3S_{22}{}^a \times (1 + I_1) + (2S_{23}{}^a + S_{44}{}^a)I_3]$$

$$S_{23}{}^y = \tfrac{1}{8}[3S_{11}{}^a I_2 + 2S_{12}{}^a I_4 + S_{22}{}^a (I_6 + I_1 -) - S_{44}{}^a I_3 - S_{66}{}^a I_2 + 6(S_{12}{}^a I_5 + S_{23}{}^a I_3)]$$

$$S_{33}{}^y = S_{22}{}^y$$

$$S_{55}{}^y = 2(S_{11}{}^a - 2S_{12}{}^a + S_{22}{}^a)I_4 + \tfrac{1}{2}[(S_{44}{}^a I_5 + S_{66}{}^a \times (I_1 + I_2 + I_3 - I_4)]$$

$$S_{66}{}^y = S_{55}{}^y$$

$$S_{44}{}^y = \tfrac{1}{2}[(S_{11}{}^a - 2S_{12}{}^a)I_2 + S_{22}{}^a(I_1 + I_6) + (S_{44}{}^a - 2S_{23}{}^a)I_3 + S_{66}{}^a(I_5 + I_4)] \tag{A8}$$

were the coefficients $I_1$ to $I_6$ can be calculated as:

$$I_1 = \tfrac{1}{2}(\cot^2\alpha)(1 - \cos^2\alpha + \sin^2\alpha) \tag{A9}$$

$$I_2 = (2\cot^2\alpha)\left(\frac{\tfrac{1}{2}}{\cos^2\alpha} + 2\ln\cos\alpha - \tfrac{1}{2}\cos^2\alpha\right)$$

$$I_3 = (2\cot^2\alpha)\ln\sec\alpha$$

$$I_4 = (2\cot^2\alpha)\left(\frac{\cos^2\alpha}{2} - \ln\cos\alpha - \tfrac{1}{2}\right)$$

$$I_5 = (2\cot^2\alpha)\left(\ln\cos\alpha + \frac{\tfrac{1}{2}}{\cos^2\alpha} - \tfrac{1}{2}\right)$$

$$I_6 = (2\cot^2\alpha)\left(\frac{\tfrac{1}{2}\sin^2\alpha}{\cos^2\alpha}\right).$$

The off-axis elastic properties of the impregnated yarn, that corresponds to the configuration of the straight fiber before coiling shown in FIG. 3(c), can be determined as follows:

$$E_x = \frac{1}{S_{11}^y},\ E_y = \frac{1}{S_{22}^y},\ E_z = \frac{1}{S_{33}^y}, \tag{A10}$$

$$G_{yz} = \frac{1}{S_{44}^y},\ G_{xz} = \frac{1}{S_{55}^y},\ G_{xy} = \frac{1}{S_{66}^y},$$

$$v_{yz} = -\frac{S_{23}^y}{S_{22}^y},\ v_{zx} = -\frac{S_{13}^y}{S_{22}^y},\ v_{xy} = -\frac{S_{12}^y}{S_{11}^y},$$

The values of $E_x$ and $G_{yz}$ to use in equations (17, 18) can then be calculated from equation (A10).

From the above modeling, artisans will appreciate that the most influential parameters to tailor a specific output contraction to design a specific elongate fiber artificial muscle with a thermal response are: fiber radius ($r_i$) and initial straight length (S), mechanical properties of the materials ($E_x$, $G_{yz}$), coefficient of thermal expansion of the matrix (CTE). For a moisture response, the coefficient of thermal expansion if replace with a coefficient of moisture expansion. The first three ($r_i$, S, $E_x$, $G_{yz}$) are useful to define the number of turns and the initial coil geometry, and the CTE is useful to determine the temperature and input energy needed to induce volume expansion. With electrical actuation, the electrical resistance R of the elongated fiber is used to calculate the value of the input voltage that causes volume expansion.

Example Applications

The elongate fiber artificial muscles of the invention have numerous applications. Preferred applications include robotics, prosthetics, orthotics, human assistive devices, morphing structures for aerial, terrestrial, and underwater vehicles. The present elongate fiber artificial muscles can substitute heavy and bulky conventional actuators (e.g., electromagnetic or pneumatic motors) many applications. They are lightweight and provide high contractile work with a small input voltage. Moreover, their flexibility, combined with the ability to finely tailor their contraction with a specific input voltage (characterized by our model described above) allows muscles of the present invention to be designed for fine and anthropomorphic motions.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. An elongate fiber artificial muscle comprising an elongate carbon or glass fiber and at least a partial coating of a polymer, wherein the polymer is volumetric ally responsive to thermal changes or to moisture changes, wherein the elongate carbon or glass fiber comprises a length that is more than tens of thousands of times that of its diameter.

2. The elongate fiber artificial muscle of claim 1, wherein the elongate fiber artificial muscle comprises a core of the carbon or glass fiber and a shell of the polymer.

3. The elongate fiber artificial muscle of claim 2, wherein the elongate fiber artificial muscle consists of the core of the carbon or glass fiber and a shell of the polymer.

4. The elongate fiber artificial muscle of claim 1, comprising a plurality of elongate carbon or glass fibers arranged together with the polymer infiltrated between the plurality of elongate carbon or glass fibers.

5. The elongate fiber artificial muscle of claim 4, wherein the plurality of fibers are twisted together with the infiltrated polymer.

6. The elongate fiber artificial muscle of claim 1, wherein the diameter is between 5 and 20 microns and the length is a half meter or more.

7. The elongate fiber artificial muscle of claim 1, comprising a power source connected to conduct current through the elongate carbon or glass fiber.

8. The elongate fiber artificial muscle of claim 7, connected at one end to an anchor point and at another end to a load to be moved.

9. The elongate fiber artificial muscle of claim 1, wherein the polymer comprises a polyether polyol.

10. The elongate fiber artificial muscle of claim 1, wherein the polymer comprises a stretchable and tough hydrogel.

11. The elongate fiber artificial muscle of claim 1, wherein the polymer comprises an oriented crystalline polymer.

12. An elongate fiber artificial muscle comprising an elongate carbon or glass fiber and at least a partial coating of a polymer, wherein the polymer is volumetrically responsive to thermal changes or to moisture changes, wherein the elongate carbon or glass fibers comprise a tow of elongate carbon or glass fibers with the polymer infiltrated within the tow.

13. The elongate fiber artificial muscle of claim 12, comprising a plurality of tows, wherein the tows are twisted together.

14. An elongate fiber artificial muscle comprising an elongate carbon or glass fiber and at least a partial coating of a polymer, wherein the polymer is volumetrically responsive to thermal changes or to moisture changes, wherein the elongate carbon or glass fiber is a PAN-based carbon fiber.

15. The elongate fiber artificial muscle of claim 14, wherein the polymer comprises PDMS.

16. A method for fabricating an elongate fiber artificial muscle, comprising:
    providing an individual elongate glass or carbon fiber or a tow of elongate glass or carbon fiber;
    coating at least part of the elongate glass or carbon fiber or the tow with a polymer precursor of a polymer that has a thermal or moisture volumetric response; and
    curing the polymer with the elongate glass or carbon fiber or tow in a predetermined artificial muscle configuration.

17. The method for fabricating an elongate fiber artificial muscle of claim 16, comprising adjusting the rheology of the polymer precursor with solvent to make it less viscous.

18. The method for fabricating an elongate fiber artificial muscle of claim 16, wherein the tow comprises a plurality of elongate glass or carbon fibers arranged together with the polymer infiltrated between elongate glass or carbon fibers.

19. The method for fabricating an elongate fiber artificial muscle of claim 18, comprising twisting the plurality of elongate glass or carbon fibers together prior to the curing.

20. The method for fabricating an elongate fiber artificial muscle of claim 19, further comprising subjecting the plurality of elongate glass or carbon fibers to tension during the twisting.

21. An elongate fiber artificial muscle comprising an elongate carbon or glass fiber and at least a partial coating of a polymer, wherein the polymer is volumetrically responsive to thermal changes or to moisture changes, wherein the elongate carbon or glass fiber has a length that is equal or greater than a length of the artificial muscle.

22. The elongate fiber artificial muscle of claim 21, comprising a plurality of elongate carbon or glass fibers arranged together with the polymer infiltrated between the plurality of elongate carbon or glass fibers, wherein each of the plurality of elongate carbon or glass fibers has length that is equal or greater than a length of the artificial muscle.

* * * * *